United States Patent
Houwen et al.

(10) Patent No.: US 8,834,400 B2
(45) Date of Patent: Sep. 16, 2014

(54) ARTIFICIAL KIDNEY

(75) Inventors: Franciscus Peter Houwen, Kronenberg (NL); Henk Van Middendorp, Achterveld (NL); Jacobus Cornelis Musters, Swifterbant (NL)

(73) Assignee: Relitech B.V., Nijkerk (NL)

( * ) Notice: Subject to any disclaimer, the term of this patent is extended or adjusted under 35 U.S.C. 154(b) by 0 days.

(21) Appl. No.: 13/467,562

(22) Filed: May 9, 2012

(65) Prior Publication Data

US 2012/0283628 A1 Nov. 8, 2012

Related U.S. Application Data

(63) Continuation of application No. 12/664,458, filed as application No. PCT/NL2008/050381 on Jun. 16, 2008, now Pat. No. 8,277,407.

(30) Foreign Application Priority Data

Jun. 14, 2007 (EP) .................................. 07110290

(51) Int. Cl.
*A61M 37/00* (2006.01)
*A61M 1/34* (2006.01)
*A61M 1/36* (2006.01)

(52) U.S. Cl.
CPC ........... *A61M 1/3472* (2013.01); *A61M 1/3486* (2014.02); *A61M 1/3672* (2013.01); *A61M 1/3468* (2014.02); *A61M 1/3489* (2014.02)
USPC ......................................... 604/5.04; 604/5.01

(58) Field of Classification Search
USPC ................ 604/5.04, 6.01, 6.04, 6.09
See application file for complete search history.

(56) References Cited

U.S. PATENT DOCUMENTS

| | | | | |
|---|---|---|---|---|
| 6,676,622 | B2 * | 1/2004 | Strahilevitz | 604/5.01 |
| 2004/0182787 | A1 * | 9/2004 | Chevallet et al. | 210/646 |
| 2005/0208487 | A1 * | 9/2005 | Burmeister et al. | 435/6 |
| 2005/0236329 | A1 | 10/2005 | Brotherton et al. | |

FOREIGN PATENT DOCUMENTS

| | | |
|---|---|---|
| EP | 0 264 695 | 4/1988 |
| WO | WO-03/077840 | 9/2003 |
| WO | WO-2004/091694 | 10/2004 |
| WO | WO-2005/025650 | 3/2005 |
| WO | WO-2007/019519 | 2/2007 |

OTHER PUBLICATIONS

Maggi et al. "Enhanced LDL Oxidation in uremic patients: An additional mechanism for accelerated atherosclerosis?", Kidney International, vol. 45 (1994), pp. 876-883.*

(Continued)

*Primary Examiner* — Philip R Wiest
*Assistant Examiner* — Benjamin Klein
(74) *Attorney, Agent, or Firm* — Miller, Matthias & Hull LLP

(57) ABSTRACT

Artificial kidney for gradual, and at least semi-continuous, blood treatment, wherein a blood stream is fed from a body of a living human or animal being into the artificial kidney, where anticoagulation is first effected, blood cells and molecules of large and medium molecular weight, such as proteins, are then primarily separated from plasma and fed back to the blood stream, regulating a water and salt balance by diverting excess plasma water and further removing from the blood stream, plasma or plasma water accumulated and toxic substances, by removal of specific electrolytes and waste products and wherein purified or partially purified plasma and plasma water is being carried back to the blood tract of the body.

8 Claims, 7 Drawing Sheets

(56) References Cited

OTHER PUBLICATIONS

Vanholder et al. "Review on uremic toxins: Classification, concentration, and interindividual variability", Kidney International, vol. 63, (2003), pp. 1934-1943.*

International Search Report for related International Application No. PCT/NL2008/050381; report dated Oct. 14, 2008.

* cited by examiner

ARTIFICIAL KIDNEY

CROSS-REFERENCE TO RELATED APPLICATIONS

This application is a continuation of U.S. patent application Ser. No. 12/664,458, filed on Mar. 10, 2010, which is a 35 USC §371 U.S. national stage filing of International Patent Application No. PCT/NL2008/050381 filed on Jun. 16, 2008, which claims priority under the Paris Convention to European Patent Application No. 07110290.9, filed on Jun. 14, 2007.

FIELD OF THE DISCLOSURE

BACKGROUND

The invention relates to an artificial kidney and, more in particular, an artificial kidney that is suitable for gradual, and at least semi-continuous, blood treatment of preferably ambulant patients.

Patients with a defective kidney function require frequent blood dialysis. During such dialysis blood is taken from the patients body for removal of uremic metabolites (N-containing protein waste products: e.g. urea and creatinine), electrolytes, waste products, accumulative substances, toxic substances, and redundant liquid, while salt concentrations are adjusted. At the same time the blood that is being returned to the patient's body needs to remain in possession of its majority of useful substances originally contained therein. There are generally two dialysis methods in common use: haemodialysis and peritoneal-dialysis. Patients treated with haemodialysis are required to visit a hospital or dialysis centre typically two or three times a week, where treatment takes typically about from 3 up to 4 hours. During treatment the patient is confined to the static location of the dialysis equipment, which causes severe discomfort to such kidney patients. Patients that can be treated by peritoneal-dialysis have their abdomen cavity rinsed typically 4 to 5 times a day with a special rinsing fluid via a catheter in the abdomen partition. Peritoneal-dialyses has the advantage that it can be performed at the patient's home, but it still requires the patient to be regularly checked in a hospital. These known methods of dialysis are intermittent and represent little more than a bad substitute for a healthy person's kidney which functions continuously for 24 hours and 7 days a week. Patients with deteriorating renal functions and chronic kidney failure thus typically suffer from chronic uremic toxicity. It should therefore not come as a surprise that in spite of the availability of dialysis, kidney patients are generally unhealthier, are continuously feeling tired and experience many side effects, such as heart and vascular diseases, diabetes, tingling, impotencies, as well as a generally shortened life expectancy. Moreover kidney patients experience much impact on their social life and psychological wellbeing, and more often than not have become unable to participate in, or contribute to economical processes. Increasing the speed of these known static dialysis processes is not an option, because removal, and return, of blood from and to a patient's body at a too rapid rate would result in cardiovascular problems. Dialysis even at the present 'slow' rate still frequently results in side-effects in the patient. One commonly experienced effect after dialysis is referred to as 'hangover'. The current dialysis methods achieve only about 10 to 20% overall clearance as compared to a healthy kidney with filtering generally being inadequate. Because of the difficulty to control liquid levels in dialysis patients there are usually large fluctuations. Kidney and dialysis patients therefore are bound to a very strict drinking and diet regime. Another difficulty is that only the extra cellular liquid of a patient can be subjected to a dialysis treatment. All intra cellular amounts of liquid can only indirectly and gradually become part of a dialysis treatment, but are not instantly treatable. Basically the currently practised forms of dialysis only offer a life-saving treatment. The patient's health status during dialysis is usually poor, because the available renal replacement treatments can at best only provide relief for part of the failing renal functions. While endocrine and homeostatic functions can be performed to a reasonable extent, the excretion of organic anions and cations, and of protein-bound middle molecules cannot be replaced by the currently performed therapies. Kidney transplantation has also been practised as a solution for patients with a permanent renal failure. Although such transplantations have often successfully restored renal functions in kidney patients, the health benefits have remained limited by the adverse effects of the necessary immunosuppressive therapy. Kidney transplantations are subject to the availability of transplantable kidneys and occasionally initially successful transplants have also failed in the course of time. Accordingly there still is a demand for more continuous forms of blood purification that include regulated excretion of excess fluid, electrolytes and uremic toxins. There thus also is a continued need for artificial kidney devices performing such purification that, at least, can be put on a table top, are wearable extracorporal by the patient in comfort or, better still, can be brought into an implantable form.

SUMMARY OF THE INVENTION

Accordingly it is an object of the present invention to overcome or ameliorate at least one of the disadvantages of the prior art. It is also an object of the present invention to provide alternative structures which are less cumbersome in assembly and operation and which moreover can be made relatively inexpensively. Alternatively it is an object of the invention to at least provide the public with a useful choice. More in particular it is an objective of the invention to provide chronic kidney patients with an improved clearance of at least one of uremic and toxic waste products, accumulated metabolites, and/or an improved water and salt balance, as well as possibly providing a generally improved mobility for the patient. It is also a particular objective of the invention to provide preservation of residual renal functions to patients not yet having a permanent kidney failure by relieving uremic stress.

To this end the invention provides an artificial kidney, including a first fluid connection; a second fluid connection; a third fluid connection; a first fluid passage extending between the first and second fluid connection, the first fluid connection defining an upstream end of the first fluid passage and the second fluid connection defining a downstream end of the first fluid passage; a second fluid passage extending from a first location on the first fluid passage, adjacent the upstream end, to a second location on the first fluid passage, the second location being adjacent the downstream end; and a third fluid passage extending from a third location along the second fluid passage to the third fluid connection, wherein the second fluid passage at the first location is connected to the first fluid passage by a first separator and the third fluid passage at the third location is connected to the second fluid passage by a second separator. The present invention recognises that it is first of all important to remove excess liquid from kidney patients. This initial embodiment of the artificial kidney according to the invention regulates only water and salt balance. Blood is separated in components, while sufficient plasma water is removed from physiologically important substances, which are being fed back to the blood tract. Excess plasma water is removed as "urine". Nephrology experts have already expressed an interest in a form of artificial kidney, as now proposed by the invention, which "only" regulates the water and salt balance, as a welcome product for dialysis patients.

Embodiments of the invention can be provided with the following particulars, either separately or in combination:

Further including a fourth fluid passage extending from a fourth location along the second fluid passage to the second location on the first fluid passage, the fourth fluid passage at the fourth location is connected to the second fluid passage by a third separator.

The fourth, location being downstream of the third location.

Further including a clearance compartment, incorporated in the fourth fluid passage.

Further including a buffer compartment, incorporated in the fourth fluid passage.

Further including a buffer compartment, incorporated in the fourth fluid passage, wherein the buffer compartment is positioned upstream of the clearance compartment.

The clearance compartment includes an absorbing material.

The clearance compartment includes an ion exchange material.

The clearance compartment includes anti-bodies.

The clearance compartment includes aptamers.

The clearance compartment includes enzymes.

The clearance compartment includes medicines.

The clearance compartment includes physiologically active cells.

The physiologically active cells comprise kidney cells.

The physiologically active cells comprise bacteria.

The clearance compartment is an exchangeable unit.

The first, second and third separators are incorporated in an exchangeable separator unit.

The clearance compartment and the separator unit are incorporated in an exchangeable cassette.

The exchangeable cassette also includes the buffer compartment of claim 5.

The ion exchange material removes any one of $K^+$ and $H_2PO_4^-$.

Further including an anticoagulant supply entrance connecting to the first fluid passage, adjacent the upstream end, for administering an anticoagulant.

Further including an antidote supply entrance connecting to the first fluid passage, adjacent the downstream end, for administering an antidote to neutralise the effect of an anticoagulant.

The clearance compartment includes a' plurality of internal fluid passages.

The plurality of internal fluid passages each include a modification station.

All or some of the modification stations are provided with a by-pass connecting a location of the relevant internal fluid passage, upstream of the modification station, with a location of the relevant internal fluid passage downstream of the modification station.

At least one of the modification stations is adapted to subject a passing fluid to modification by an agent selected from a group including: an absorbing material, an ion exchange material, anti-bodies, aptamers, enzymes, medicines and physiologically active cells.

A fluid flows through at least one of the first, second, and third fluid passages can be controlled by flow control means selected from a group including pumps, valves, restrictors, pressure regulators, and flow regulators, each controlled by a control device.

At least one of the first and second separators are selected from a group including centrifugal separators and filter systems.

The second and third separator are formed by filter systems.

According to a further aspect of the invention the artificial kidney, further includes a fourth fluid passage extending from a fourth location along the second fluid passage to the second location on the first fluid passage, the fourth fluid passage at the fourth location is connected to the second fluid passage by a third separator and preferably also further includes a clearance compartment, incorporated in the fourth fluid passage. In this further embodiment a clearance compartment is added. In this clearance compartment toxic and accumulating substances are removed by means of adsorption, enzymes and/or living cells. Plasma water after possible extra filtration can also be lead via an ion exchange composite and subsequently be carried back to the blood tract. This enhanced version of the invention recognises the importance of removing substances that are known to be toxic when present in too high concentrations. The substances include sodium ($Na^+$), potassium ($K^+$) and phosphate ($H_2PO_4^+$), which are important to be removed. Controlled removing of these substances is carried out with an appropriate selection of the capacity of ion exchange composites.

With the initial and further embodiments of the invention the need for haemo-dialysis or peritoneal dialysis at regular intervals, for removing other objectionable substances from the patient's blood, may still, not be completely eliminated. However in-between these treatments a larger degree of health and a much improved quality of live for the kidney patient can be achieved.

A further refined embodiment of artificial kidney according to the invention further includes a buffer compartment, incorporated in the fourth fluid passage, wherein the buffer compartment is positioned upstream of the clearance compartment. Preferably it also includes at least one sensor for determining a physical characteristic, including chemical and biochemical characteristics, of a fluid passing through the artificial kidney, a control device in communication with the at least one sensor and one, or more, flow control means selected from a group including pumps, valves, restrictors, pressure regulators, flow regulators and agent administering devices. The clearance compartment preferably is incorporated in an exchangeable cassette. By adding a buffer compartment this further refined embodiment can further benefit from additional channels in the clearance compartment, each with a specific disposable material or a material that can be regenerated. Several more refined adsorption processes can be employed and automatically controlled. Also nano-filtration processes and the use of nano membranes is envisioned. With the artificial kidney according to this further refined embodiment conventional periodic haemo-dialysis or peritoneal dialysis, may in nearly all cases become superfluous.

The invention also provides a method of gradual, and at least semi-continuous, blood treatment in an artificial kidney as specified herein above, wherein a blood stream is fed from a body of a living human or animal being into the artificial kidney, where anticoagulation is first effected, blood cells and molecules of large and medium molecular weight, such as proteins, are then primarily separated from plasma and fed back to the blood stream, regulating a water and salt balance by diverting excess plasma water and further removing from the blood stream, plasma or plasma water accumulated and toxic substances, by removal of specific electrolytes and waste products and wherein purified or partially purified plasma and plasma water is being carried back to the blood tract of the body.

The method of the invention can further be provided with the following particulars, either separately or in combination:

The electrolytes and waste products are removed by means selected from a group comprising adsorption, enzymes and living cells.

Clearance is accomplished with means selected from a group comprising ion exchangers, antibodies, aptamers, enzymes, molecular imprinting recognition or other materials.

Specific electrolytes and waste products are removed by adsorption in a quantity determined by a selected capacity of an adsorbing material.

Specific electrolytes and waste products are removed in a quantity determined by measuring concentrations of the electrolytes and waste products, using a control device for regulation.

Selected substances, such as medicines, are added to plasma water, in a controlled manner.

Control of pH is performed by measuring concentration of $H^+$ ions in the plasma water and controlled dosing to the plasma water of $H^+$, $OH^-$ ions or acetate by means of a control device in response to the measured concentration.

Anticoagulation is performed by a citrate and the anticoagulation is being cut, by adding of $Ca^{2+}$ ions.

The $Ca^{2+}$ ions are added in a clearance compartment, by means of a control device.

$Ca^{2+}$ concentration is regulated by ion exchangers.

Substances are administered to the blood or plasma after the primary separation and before return of the blood or plasma into the blood tract of the body.

The substances are selected from a group comprising medicines, $H^+$ ions, $OH^-$ ions, $Ca^{2+}$ ions and antidotes.

The invention also envisions general methods of temporarily inactivating thrombcytes by using an aptamer and/or of anticoagulation of whole blood using aptamers. This can be carried out independently of blood treatment in an artificial kidney or in conjunction with artificial organs other than artificial kidneys.

BRIEF DESCRIPTION OF THE DRAWINGS

The invention will now be further explained in reference to selected embodiments as illustrated in the accompanying drawings in which.

DETAILED DESCRIPTION OF THE DRAWINGS

Figure 1:
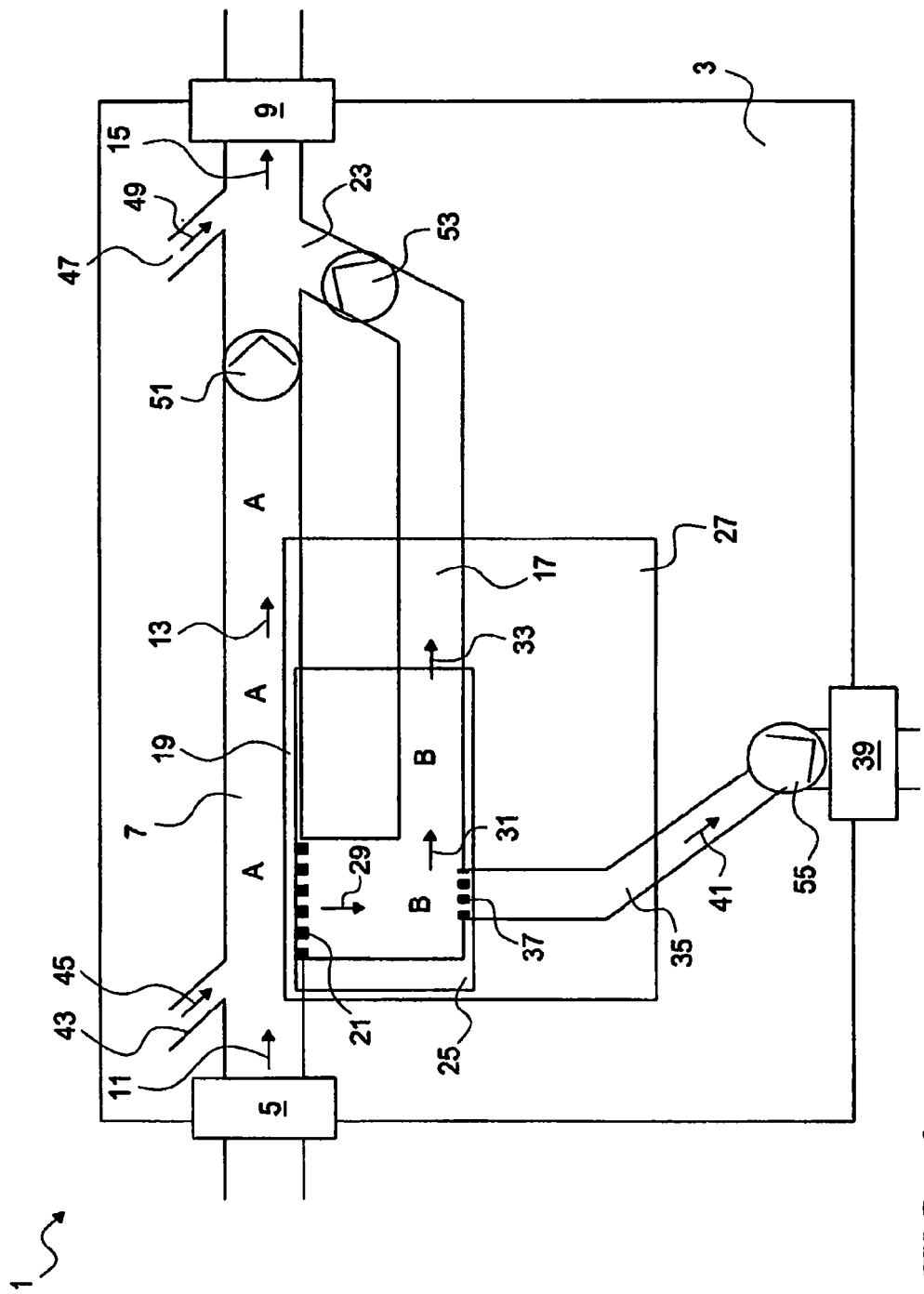
FIG. 1 is a schematic representation of a first embodiment of artificial kidney according to the invention.

FIG. 1 schematically shows a first embodiment of artificial kidney 1. This is shown to have a housing 3 that can be either a table top version, a version wearable on a patient body or alternatively a version implantable in a patient's body. The housing has a first sterile fluid connection 5 to receive blood "A" from the patient. A first fluid passage 7 extends from the first fluid connection 5 to a second sterile fluid connection 9 from which blood "A" can re-enter the patient's blood track. The first fluid connection 5 defines an upstream end of the first fluid passage 7 and the second fluid connection 9 defines a downstream end of the first fluid passage 7. The direction of the blood flow "A" is indicated by arrows 11, 13, 15. This blood flow "A" amongst others contains blood cells, proteins, creatinine, urea, electrolytes and water. A second fluid passage 17 extends from the first fluid passage 7 from an upstream location 19 and is in fluid communication with the first fluid passage 7 by means of a first separator 21. This first separator 21 is schematically represented as a filter, but in practise can also be formed as a centrifugal separator. The second fluid passage 17 extends towards a second location 23 on the first fluid passage 7 adjacent to the downstream end defined by the second fluid connection 9. At least a first part of the second fluid passage 17 extends through a filter unit 25, which is part of an exchangeable cassette 27. Through the first separator 21 some blood plasma "B" is separated from the blood flow "A". The blood plasma B has been separated from blood cells and (preferably) large molecules like proteins, which remain in the main flow A. The blood plasma flow B amongst others still contains proteins, creatinine, urea, electrolytes and water and generally flows in the direction of arrows 29, 31, 33. A third fluid passage 35 is in fluid communication with the second fluid passage 17 through a second separator 37. The third fluid passage 35 connects to a third fluid connection 39, which forms an exit for surplus liquid separated in the form of plasma water from the blood plasma flow B. In the case of the third fluid passage 35 the separator 37 defines an upstream end and the third fluid connection 39 defines a downstream end thereof. The resulting fluid flow direction of the third fluid passage 35 is indicated by arrow 41. The third fluid connection 39 may discharge either into an exchangeable receptacle or into the bladder of the patient. The first fluid passage 7 is further provided with an upstream entrance 43 for the supply of an anticoagulant to the blood stream A. The supply of this anticoagulant is represented by arrow 45.

It is envisioned that this anticoagulant can be a conventional citrate, which can be neutralised, before the blood is returned to the patient, by administering $Ca^{2+}$ ions. When it is necessary to use such or other antidotes to neutralise anticoagulants, a downstream entrance 47 is optionally provided in the immediate vicinity of the second fluid connection 9. The supply of antidote is represented by an arrow 49.

In one preferred variation of the invention the anticoagulant is a suitable aptamer such as those proposed in United States patent publication US 2005/176940 or U.S. Pat. No. 5,840,867. It is possible for such aptamers to have a limited duration of effectiveness as anticoagulants. It is also possible for such aptamers to have their effectiveness rapidly diminished once dissolved in the patients blood track. Several ways of controling the affinity and specificy of the aptamer, or the aptamers, by varying their environmental conditions are known. These notably include: using light of a specific frequency; adding to the solution of aptamers one or more substances for example one or more electrolytes or one or more small proteins; or altering of temperature. Accordingly it is possible with such aptamers to remove their affinity by exposure to light of a specific frequency, as described by Heckel et al. ("An anticoagulant with light-triggered antidote activity", Angewandte Chemie—International Edition, Vol. 45, no 40, pp/6748-6750, Wiley—VCH Verlag GmbH & CO KGaA, Weinheim 2006. Also of particular intrest are the examples disclosed by: Nimjee, Shahid M, Rusconi; Christopher P; Harrington, Robert H; and Sullenger, Bruce A: "The potential of aptamers as anticoagulants" (Trends in Cardiovascular Medicine, Vol. 15, Issue 1, January 2005, pp 41-45). In all the latter examples the downstream entrance 49 for the supply of an antidote 49 can be suppressed.

Also shown in FIG. 1 is a first flow control means 51 which can be optionally included in the first fluid passage 7.

The first flow control means 51 can be selected from a group including pumps, valves, restrictors and pressure regulators. In the illustrated embodiment the flow control means 51 is represented as a pump. In a preferred arrangement the pumping rate of such a pump 51 can be varied by electronic means, which variation of pumping rate may even include the inversion of the pumping direction. Such a flow control means will enable full control over the flow, at any moment, of blood A in the first fluid passage 7 and thereby over the amount of blood plasma that passes through the first separator 21 into the second fluid passage 17. It is further seen that the second fluid passage 17 can also optionally be equipped with a second flow control means 53. The second flow control means 53, when in a similar form as the first flow control means 51 (such as a pump), can be controlled in conjunction therewith, so that the blood flow 15 leaving the second fluid connection 9 accurately matches the blood flow 11 entering at the first fluid connection 5. In this context it should be clear that the return flow at 15 does not always need to be identical to the incoming flow 11. There could be medical reason to administer back to a patient either a somewhat lower or a somewhat higher blood flow than the flow of blood that is extracted from the patient.

An electronic control of the first and second control means 51, 53 could be structured to also govern parameters sampled from the patient's body. It follows that a basic control over the flow of plasma water through the third fluid passage 35 via the separator 37 can also be controlled by the combined operation of the first and second flow control means 51, 53 if operated in conjunction with one another. It can however be preferred in an optional arrangement to include a third flow control means 55 in the third fluid passage 35 to give additional control over the amount of plasma water leaving the third fluid connection 39 and thereby giving further control over the amount of blood plasma B that is returned to the first fluid passage 7 for return to the patient's body via the second fluid connection 9.

Figure 2:
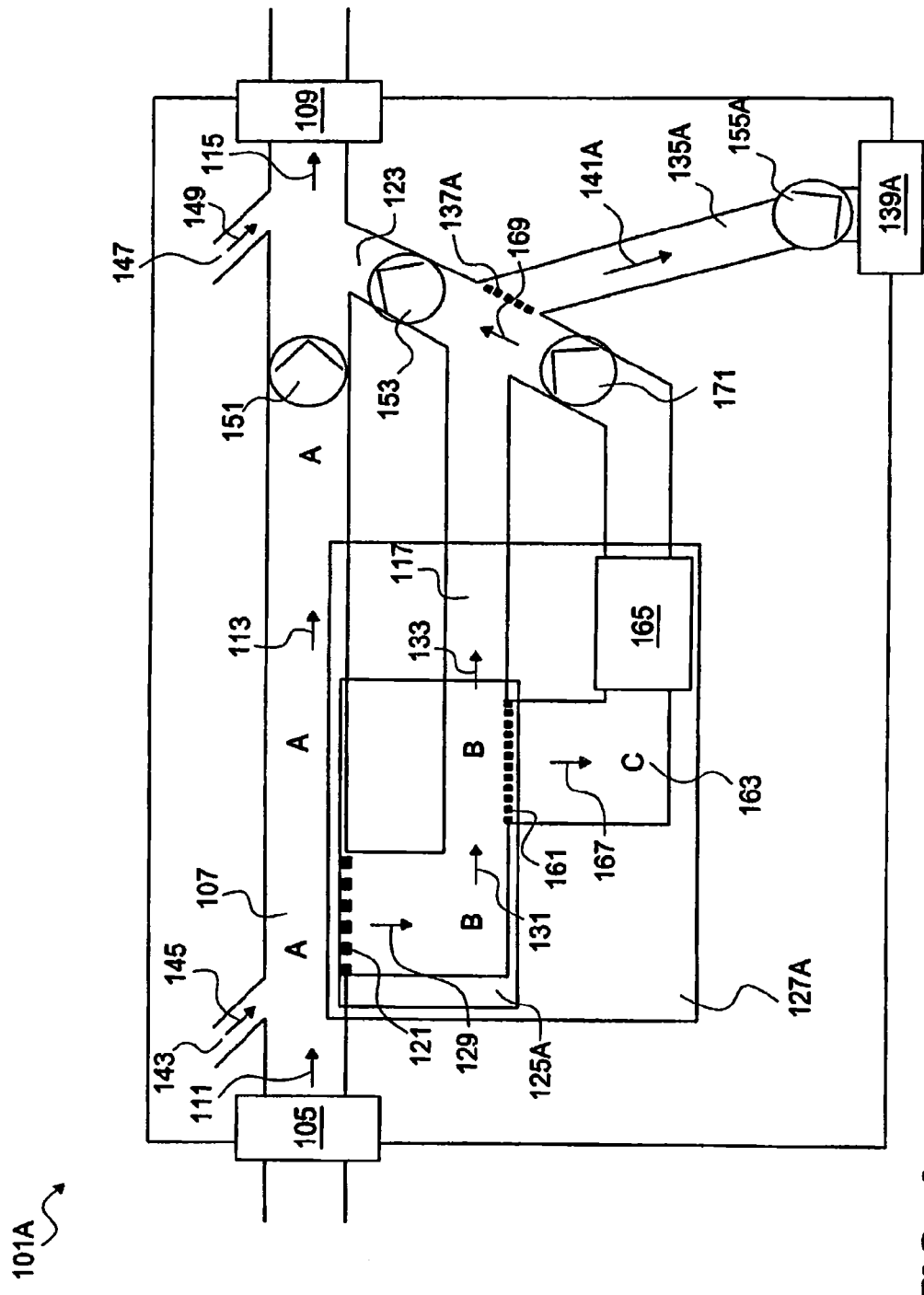
FIG. 2 is a schematic representation of a second embodiment of the invention.

FIG. 2 schematically shows a second embodiment of the invention. All elements similar to the first embodiment have been given reference numbers that differ a full "100" from those used in FIG. 1. For all purpose and intent reference is made to the description of FIG. 1 for any further detail of these common elements if not elaborated on below. The artificial kidney 101A of FIG. 2 has a first fluid connection 105 for receiving blood A from a patient. A first fluid passage 107 extends from the first fluid connector to a second fluid connection 109. The blood flow A generally flows in the direction of arrows 111, 113, 115 from and back to the patient's body. A second fluid passage 117 extends again from the first fluid passage 107 from an upstream positioned first separator 121 by means of which it is in fluid communication with the first fluid passage 107. The second fluid passage has a feed back connection to the first fluid passage 107 at a downstream location 123, via an optional flow control means 153. The second fluid passage 117 is adapted to be filled with blood plasma B, without the blood cells and preferably large molecules that have been blocked by the first separator 121. Those blood cells remain in blood stream A and will be returned to the patient's body. The blood plasma B flows generally in the direction of arrows 129, 131 and 133. A third fluid passage 135A, which represents a plasma water drain to the third fluid connection 139A has a slightly different position as opposed to the first embodiment but functions substantially similar. The third fluid passage 135A is in similar fluid communication with the second fluid passage 117 by means of a second separator 137A and can again optionally include a third flow control means 155A in its traject towards the third fluid connection 139A. The second embodiment 101A also has a filter unit 125A, which in this case does not include the separator 137A, but instead a third separator 161 which is in communication with a fourth fluid passage 163. The fourth fluid passage 163 is in fluid communication with a clearance compartment 165. At least a portion of the fourth fluid passage 163 enters the clearance compartment 165. The clearance compartment 165 and the filter unit 125A are integrated into an exchangeable cassette 127A. A stream of plasma water C which, inter alia, still contains accumulated concentrations of creatinine, urea and/or electrolytes flows through the fourth fluid passage 163 in the direction of arrow 167. After leaving the clearance compartment 165 the flow of plasma water is fed back to the second fluid passage 117 in accordance with arrow 169. The flow of stream C through the clearance compartment 165 can optionally be controlled by a fourth flow control means 171. The clearance compartment 165 is arranged to subject the plasma water C to any appropriate combination of agents selected form a group including: absorbing material, ion exchange material, anti-bodies, aptamers, enzymes and physiologically active cells, e.g. kidney cells or bacteria. It is also an option of the clearance compartment 165 to subject the plasma water to medicaments which is subsequently fed back to the patient's body.

In reference to FIG. 2 aptamers may also be used for reversibly binding substances in the clearance compartment. By binding to aptamers, it becomes possible to regenerate the clearance compartment in an intermittently performed cycle. The resulting waste products can then be allowed to leave the artificial kidney by means of the third fluid connection 139A, controlled by pumps 153 (interrupted or closed), 171 and 155A. Such an intermittently applied regeneration cycle can also be applied to other parts of the artificial kidney.

Figure 3:
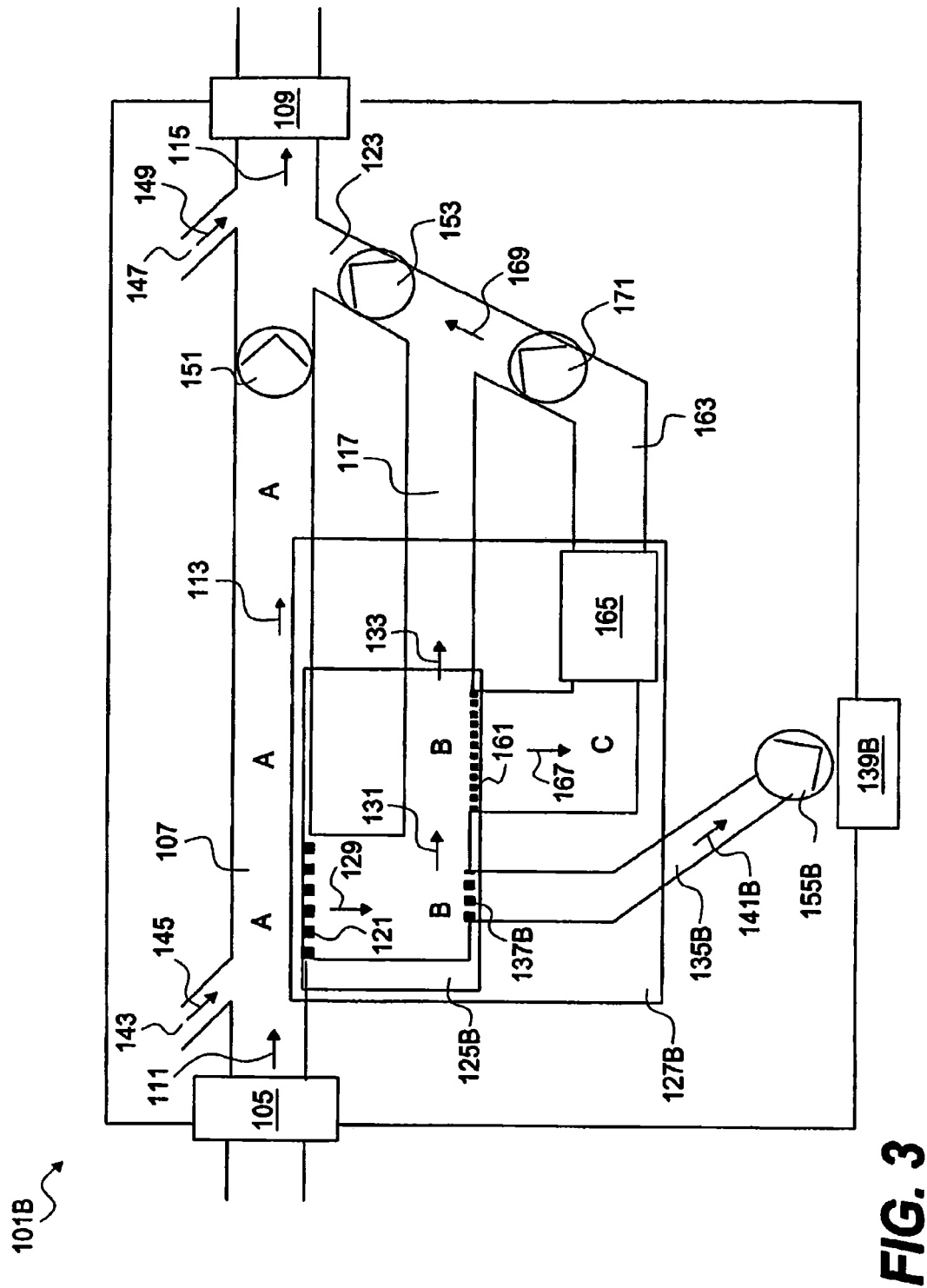
FIG. 3 is a schematic representation of a modification of the second embodiment.

FIG. 3 relates to a slightly modified form of the second embodiment 101B except for the position of the third fluid passage 135B and the arrangement of the filter unit 125B and exchangeable cassette 127B, the modified second embodiment of artificial kidney 101B is identical with that discussed in reference to FIG. 2. The position of the third fluid passage 135B and the second separator 137B in the filter unit 125B is again identical to the arrangement discussed in reference to FIG. 1. A detailed discussion of FIG. 3 is therefore deemed superfluous. The second embodiment of the invention without using of a dialysate (rinsing fluid) as in some previously proposed wearable artificial kidneys can adequately regulate the water and salt balance and moreover ensure to some extent that a sufficient clearance is carried out of toxic and accumulating substances from blood. This artificial kidney can easily take the form of a portable basic unit in wearable format with a disposable cassette.

Figure 4:
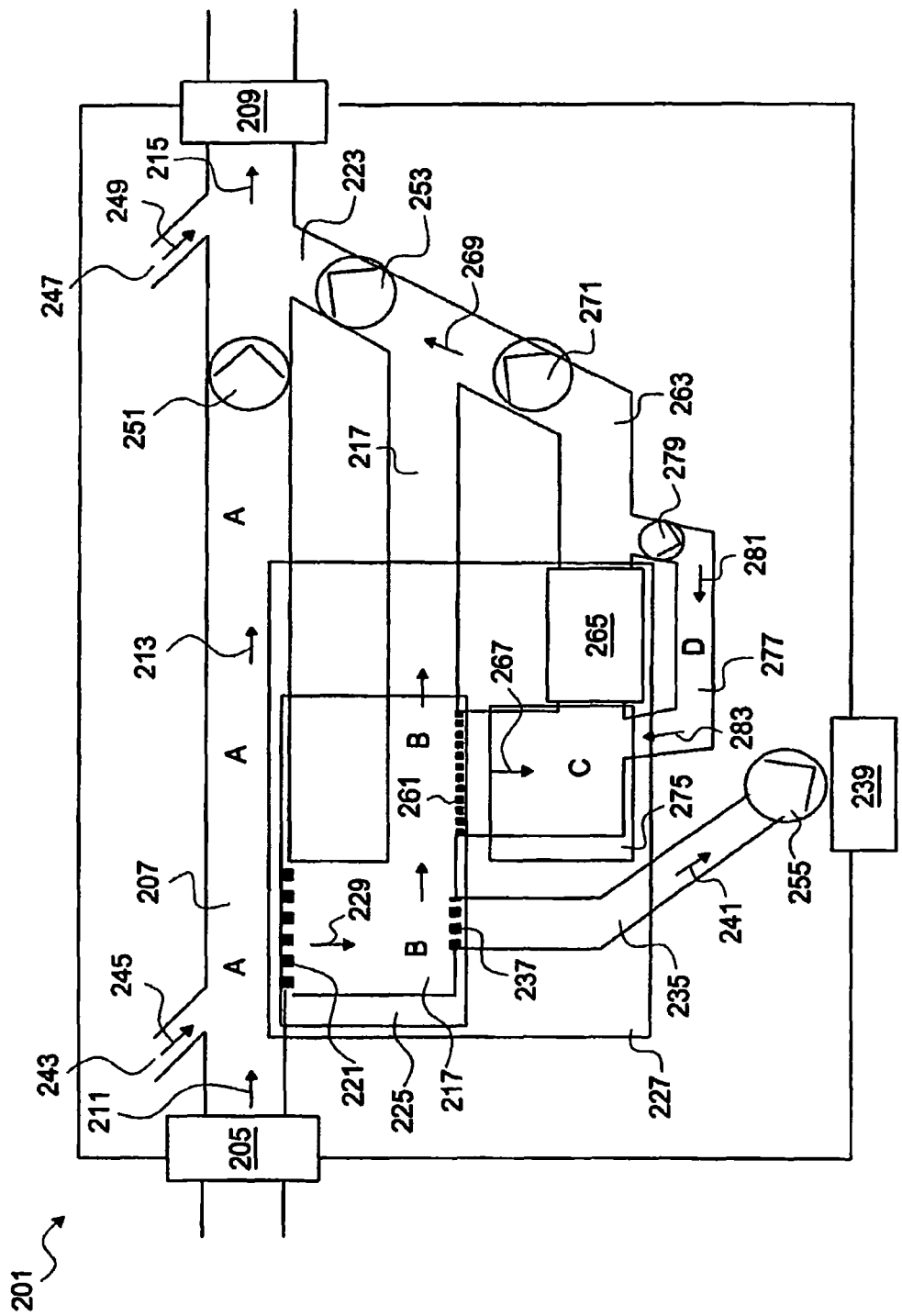
FIG. 4 is a schematic representation of a third embodiment of the invention.

FIG. 4 schematically shows a third embodiment of artificial kidney 201. Elements similar to those of the first embodiment have been given reference numbers that differ a full "200" with those used in FIG. 1. Similarly the elements similar to those of the second embodiment have been given reference numbers a full "100" higher than those used in FIGS. 2 and 3. For any details of the common elements not discussed herein below reference is made to the description above. The third embodiment of artificial kidney 201 is additionally provided with a buffer compartment 275, which is part of the fourth fluid passage 263 and positioned upstream of the clearance compartment 265. Downstream of the clearance compartment 265 there is a return fluid passage 277 connected to the fourth fluid passage 263, which leads back into the buffer compartment 275. Flowing through this return fluid passage 277 is plasma water D that has been treated by the clearance compartment 265, but which still may contain too high concentrations of residual creatinine, urea and/or electrolytes. With the optional assistance of a fifth flow control means, such as a pump 279, the return flow of plasma water D flows through the return passage 277 in the direction of arrows 281, 283. The remainder of what is shown in FIG. 4 is substantially similar to FIG. 3. The artificial kidney 201 has again a first fluid connection 205, a second fluid connection 209 and a third fluid connection 239. The first fluid passage 207 extends between the first and second fluid connections 205, 209 and the blood flow A generally follows the arrows 211, 213 and 215. The second fluid passage 217 extends from a first separator 221 in fluid communication with the first fluid passage 207, toward a downstream connection with the first fluid passage 207. The third fluid passage 235, which is a plasma water drain, extends from a second separator 237, in fluid communication with the second fluid passage 217, towards the third fluid connection 239. The buffer compartment 275 is in fluid communication with the second fluid passage 217, through the third separator 261 and also with the clearance compartment 265 and fluid return passage 277. First, second, third, fourth and fifth flow control means (251, 253, 255, 271 and 279) can again be optionally included in the various fluid passages to control the amount of fluid passing the first, second and third separators (221, 237, 261) as well as the clearance compartment 265.

Figure 5:
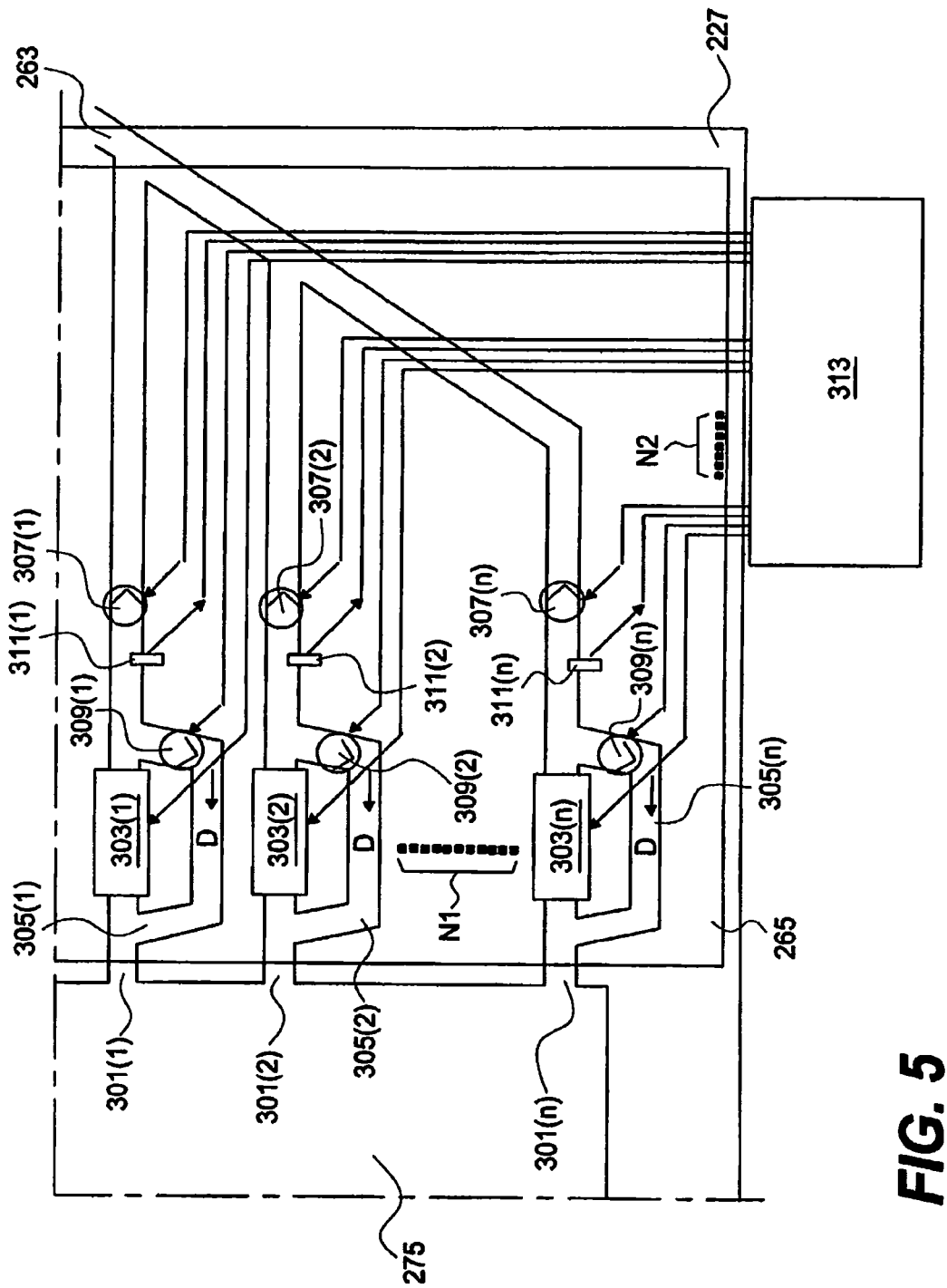
FIG. 5 is a schematic enlarged detail of a clearance compartment for use with the third embodiment according to FIG. 4.

FIG. 5 is an enlarged schematic detail of the exchangeable cassette 227, showing the clearance compartment 265 of the third embodiment of FIG. 4. While this is the case, it is also emphasized at this point that certain aspects of the clearance compartment 265 can also be employed in the clearance compartment 165 of the second embodiment. The clearance compartment 265 includes a plurality of internal fluid passages or channels 301(1), 301(2) ... 301(n) (n being any appropriate number). Each internal fluid passage 301(1), 301(2), ... 301(n) includes a fluid treatment of modification station 303(1), 301(2) ... 303(n), which each can contain a specific one of various substances for removing undesirable contaminations from the plasma water. Each fluid treatment station 303(1), 303(2), ... 303(n) is associated with a fluid return passage 305(1), 305(2) ... 305(n), which connects a portion of the relevant internal fluid passage 301(n) downstream of the fluid treatment station 303(n) with a portion of the internal fluid passage 301(n) upstream of the fluid treatment station 303(n). Alternatively the return passages 305(n) can also connect to the buffer compartment 275 upstream of the fluid treatment stations 303(n). The flow through each of the internal passage 301(n) can be controlled by a relevant flow control means 307(1), 307(2)...307(n). Likewise return flow control means 309(1), 307(2) ... 307(n) are preferably provided in each return fluid passage 305(n) for precisely controlling the amount and duration of the fluid flowing through the treatment stations 303(n). The dotted lines N1 and N2 in FIG. 5 represent any optional number of channels, containing an internal fluid passage 301(n) having a treatment station 303(n) and a fluid return passage 305(n). The clearance compartment 265 of FIG. 5 further includes a sensor 311(1), 311(2)...311(n) in each internal fluid passage 301(n) to determine the quality of the fluid that has passed the particular treatment station 303(n). The location of the sensors 311(1), 311(2) ... 311(n) can be somewhere in the loop formed by each fluid passage 301(n) and its associated return passage 305(n), or be downstream of the relevant treatment station 303(n). A signal or value produced by each sensor is offered to a control device 313, which may contain a micro processor and which evaluates the communicated signals or values. Subject to this evaluation by the control device 313 control signals are generated and send to electronically controllable devices such as the various flow control means 307 (n), 309(n), and to the treatment stations 303(n) in the clearance compartment for the control or adjustment of flows and treatments. The control unit 313 preferably is also arranged to control the first, second, third, fourth and fifth flow control means 251, 253, 255, 271 and 279 of the entire artificial kidney 201 (or 101 in the case of the second embodiment). The treated plasma water leaves the clearance compartment via the downstream part of the fourth fluid passage 263. Generally each sensor 311(n) determines a physical characteristic of the fluid that has passed a treatment station 303(n) and the control device 313 in communication with the sensors 311(n) controls the operation of appropriate fluid control means, such as 307(n) and 309(n). The processes described in reference to FIGS. 4 and 5 take place entirely within the disposable cassette 227, but in different embodiments of the invention to arrange at least some of these processes to be carried out in the main unit of the artificial kidney.

In use the artificial kidney according to the described embodiments of the invention will primarily separate blood cells and large molecules from blood plasma. Further sequential filtration finishes with micro filtration or possibly nano filtration. The plasma water filtered in this way is cleared using several adsorption materials, enzymes and/or living cells. Moreover certain substances will be specifically intercepted. Partially filtered plasma water is removed as "urine". The fluid flow in the artificial kidney will be operatively controlled by varying flow rates and pressures. This can be achieved by means of pumps, valves, restrictors, pressure regulators and flow regulators—as already explained in the preamble to this specification. A portion of the main stream (flow A) is diverted through the first separator (flow B) by means of creating a pressure differential or by temporarily obstructing the fluid flow A. Fluid flow C is created in an analogous manner using a pressure differential. Additionally (in the third embodiment) flow C is allowed to fill the fluid buffer (275) upstream of the clearance compartment (265) where specific substances are removed from the plasma water.

A first functionality of this artificial kidney is the separation of blood cells and large molecules from blood plasma. This blood plasma, after separation, still contains an amount of proteins, metabolic waste products and electrolytes. The separated blood cells and large molecules are carried back directly to the blood tract. This primary separation can be carried out by aphaeresis (centrifugation), filtration or also by using aptamers. Apart from blood cells also large molecules, such as proteins, are removed from the plasma. With subsequent micro filtration, and/or separation by aptamers, plasma water is obtained from this plasma, where also now the physiologically important molecules of large and medium molecular weight can be directly returned to the patient's blood tract.

After sequential separation has sufficiently removed physiologically important substances from plasma water (and carried back into blood tract), the remaining liquid can be removed as "urine". With this continuous or semi-continuous removal of "urine" in the order of 1000-1500 ml per day, the water- and salt balance can be regulated almost entirely. For uremic waste products and electrolytes which for a majority are intracellular, such as $K^+$ and $H_2PO_4^-$, the clearance from blood (plasma water) in the aforesaid manner is not nearly sufficient. For removing these and other substances an extra purification step is necessary.

After a secondary separation by means of filtration, and/or separation by aptamers, plasma water is allowed to flow via the fluid buffer into the clearance compartment, containing amongst others adsorbing material. The clearance compartment includes several channels which each contain individual ion exchangers or other (specific) materials. The clearance in these channels can happen both physically and chemically, for example by means of ion exchangers, and biologically by means of, for example, antibodies, aptamers, enzymes or other materials. Ion exchangers, for example, exchange $K^+$ against $Na^+$ or $H_2PO_4^-$ against $Cl^-$. Apart from $K^+$ and $H_2PO_4^-$, thereby also toxic and accumulative substances are removed from the plasma water. The filtered plasma water is returned to the blood tract.

By measuring concentrations in loops of individual substances, the flows through the channels can be controlled by means of a control device in such a manner that a correct and efficient clearance of the different substances takes place. The necessary sensors can be either included in the disposable cassette or be part of the basic artificial kidney unit.

The invention offers the additional option of regulating the pH balance of the plasma water. This control can be effected through the use of an ion exchanger which exchanges, e.g. $Na^+$ or $K^+$ against $H^+$ or which exchanges for example $H_2PO_4^-$ against $Ac^-$. Another addition which is appropriate for the described concept, is the possibility e.g. of administering medicines or drugs in one or more of the channels in the compartment, so that these can flow into the patient's blood. Also $Ca^{2+}$, as a cutting (eliminating) agent against the anti-coagulant citrate, could be added this manner.

Anticoagulation is necessary before the blood of the patient is treated in the artificial kidney (by primary separation) to prevent coagulation (concretion). This is achieved by administering anticoagulants. The coagulation must be continuously maintained, without endangering the patient with haemorrhage complications. Relative and absolute overdosing can lead to life-threatening haemorrhages.

A much applied anticoagulant is citrate. $Cit^{3-}$ binds to $Ca^{2+}$ so that this important intermediary in the cascade of the coagulation process is removed. This reaction is very quick and the effect of $Cit^{3-}$ can be cut by administering of $Ca^{2+}$ before plasma and/or plasma water is returned to the blood tract. $Cit^{3-}$ and $Ca^{2+}$ are body-own substances and have no nasty side effects. The use of citrate in combination of $Ca^{2+}$ must however be carried out very accurately to prevent complications from occurring. The $Ca^{2+}$ needs to be measured very precisely and continuously. Another possible anticoagulant is heparin. This agent offers the advantage that, apart from being able of being cut (with protamine), it also is not very stable in blood. A correctly low dosing must then be effected.

Aptamers are a very promising form of anticoagulants formed as short single strand nucleic acids (DNA or RNA), which adopt particular configurations (three-dimensional form). These bind to a specific target molecule with high affinity and specificy and can be used, for example, as potent inhibitors. Aptamers have been made, amongst others, against coagulation factor IXa and against thrombin to name only a few examples. Both these examples are key molecules in the cascade of reactions leading to blood coagulation. Aptamers are suitable candidates as anticoagulants, particularly in the artificial kidney of the invention. Aptamers can be dosed to the blood in solved condition prior to the primary separation. To the solution of the aptamer or aptamers, is also added one or more components, which upon addition to a small volume of blood in the artificial kidney take care of the correct environment for the aptamer or aptamers, so that these posses their high specificy and affinity, for a particular coagulation factor. In the artificial kidney coagulation is prevented by the presence of the aptamer or aptamers in blood (main stream A; in the described embodiments), or by the absence of some coagulation factors in plasma and plasma water (flows B and C of the described embodiments). Eliminating the anti-coagulating effect of the aptamer or aptamers evolves automatically upon return of the blood in the blood tract. The aptamers can as such be selected so that a certain component or certain components must be present in the direct surroundings of the aptamer or aptamers in a sufficiently high concentration. Blood that returns from the artificial kidney becomes sufficiently dissolved to allow the binding of the aptamer or aptamers to disappear. The aptamers are sufficiently rapidly demolished by nucleases present in blood, so that accumulation in blood does not occur. Removing the affinity of the aptamer or aptamers can also be accomplished by application of light of a particular frequency, such as described already by Heckel et al. ("An anticoagulant with light-triggered antidote activity", Angewandte Chemie—International Edition, Vol. 45, no 40, pp/6748-6750, Wiley—VCH Verlag GmbH & CO KGaA, Weinheim 2006). Yet other suitable applications of aptamers in anticoagulation are disclosed by: Weitz, Jeffrey I. and Hirsch, Jack; "New Anticoagulant Drugs" (CHEST, 119, January 2001, Supplement, pp 95S-107S); U.S. Pat. No. 6,780,850; Nimjee, Shahid M, Rusconi; Christopher P; Harrington, Robert H; and Sullenger, Bruce A: "The potential of aptamers as anticoagulants" (Trends in Cardiovascular Medicine, Vol. 15, Issue 1, January 2005, pp 41-45); and Di Guisto, D A and King, C G: "Construction, stability and activity of multivalent circular anticoagulant aptamers" (Journal of Biological Chemistry, Vol. 279, no. 45, pp 46483-46489). The aforementioned references are considered as an integral part of the present disclosure. Aptamers are typically delivered by parental administration (intravenous or intramuscular). Aptamers can possess a very short or sustained half-life; their pharmokinetic properties are adjustable (antidotes can be rationally designed to control the pharmacologic effects) and less monitoring is likely to be needed compared to e.g. heparin. Aptamers further are purported to be non-immunogenic and their lack of antigenicity has been supported by recent clinical studies (2002, 2003 and 2004). Two aptamer-based anticoagulant agents in development are designed specifically to meet the need for rapid-onset, rapid-offset agents: (i) selection of an aptamer with a very short half-life (governed by the concentration of the aptamer) and (ii) adding of an antidote (binds to an aptamer that thereby loses its 3-dimensional structure). Aptamers in particular exhibit several properties that make them potentially quite suitable for use as anticoagulans: (i) high affinity; (ii) specific binding to their target protein; (iii) dissociation constants in the concentration range (high) pM-(low) nM; (iv) specificity constants (ratio) of $>10^3$; and (v) half-life of aptamers (in blood) can be prolonged as explained in the above referenced sources. A further possible application of aptamers in the artificial kidney of the invention are physical binding aptamer or aptamers on one of the components of the primary separation or on a surface upstream of the primary separation. The aptamers bind one or more coagulation factors which can be removed with the disposable cassette or be regenerated in situ, i.e. in case of an implantable artificial kidney. With certain of these options the patient's body can be relied on to produce the necessary replacement coagulation factors in sufficient amounts.

The described aptamer technology can also be applied to processes other than anticoagulation in the artificial kidney. Aptamers can also be applied to adsorb cells or substances. The tie of such cells or substances can be made reversible or irreversible. One option is separating blood cells from plasma by reversibly tying to aptamers. By a change of the direct environment (concentration of a particular substance or particular substances) the cells are again released. By reversibly binding substances to aptamers, it also becomes possible to regenerate the aptamers in the artificial kidney. Irreversible binding can be followed by disposal with a disposable cassette, or the like.

In a preferred form the invention can provide a compact, light weight, wearable artificial kidney that is provided with a basic unit and an exchangeable, conveniently disposable, cassette for gradual control of water and salt balance and for removing of accumulated and toxic substances from blood, where the blood is transported by means of a pump from a body of a living human or animal being to the preferably wearable artificial kidney, wherein anticoagulation is effected, followed by sequential separation of blood cells and molecules of large and medium molecular weight, such as proteins, which are separated from plasma, thus obtained plasma water is transported to a clearance compartment via a liquid buffer compartment; specific electrolytes and waste products are removed from the plasma water in the clearance compartment by means of adsorption, removal or biochemical conversion; adsorption is accomplished with ion exchangers, antibodies, aptamers, enzymes, molecular imprinting recognition or other materials; and wherein at least partially purified plasma and plasma water, are being carried back to the blood tract. The absorption by molecular imprinting recognition is a technique of creating recognition sites in polymeric materials. Successful applications of this technique have been based on cross-linked organic polymers such as polyacrylates and polystyrenes. In use molecules identical to an original template will fit into the recognition sites, created in the polymeric materials, and are bound strongly, while molecules that differ in structure are unable to bind.

Figure 6:
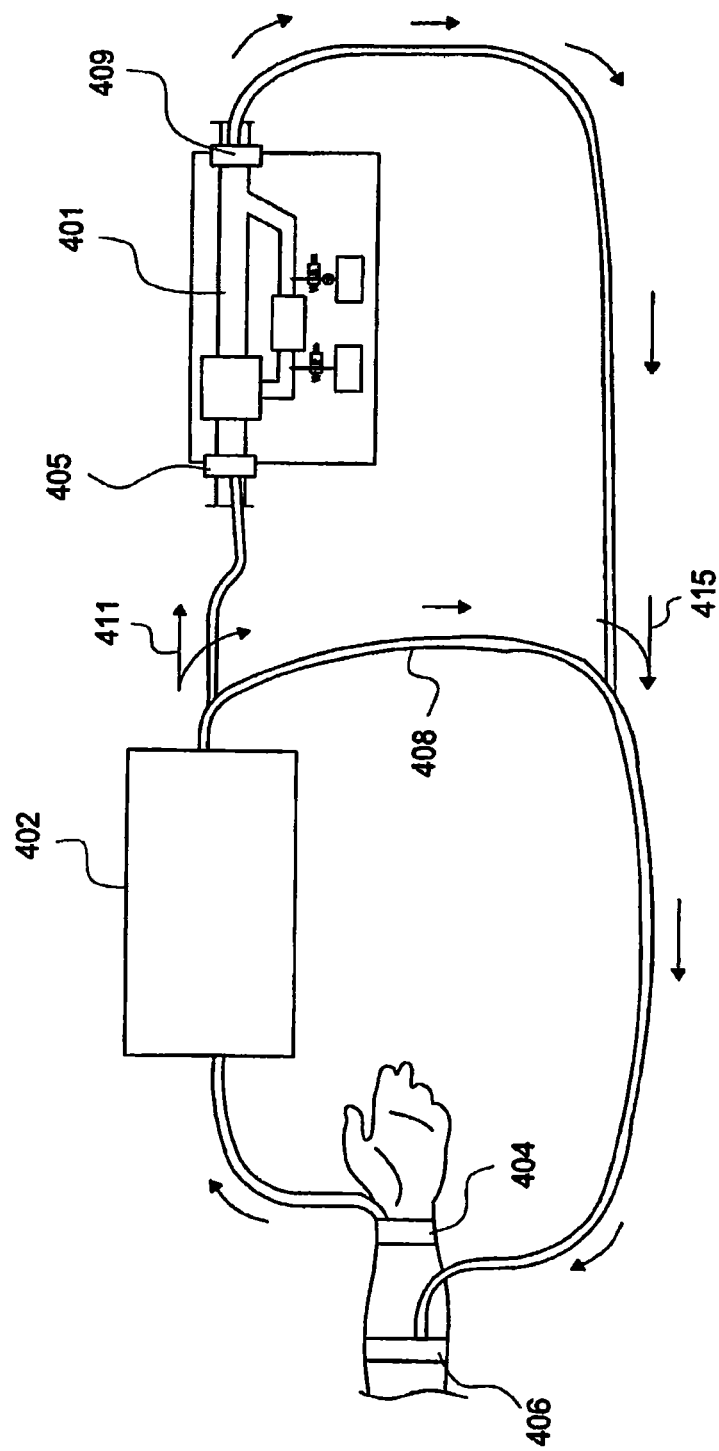
FIG. 6 is an embodiment for adjunctive blood detoxification being used in combination with existing haemo-dialysis.
Figure 7:
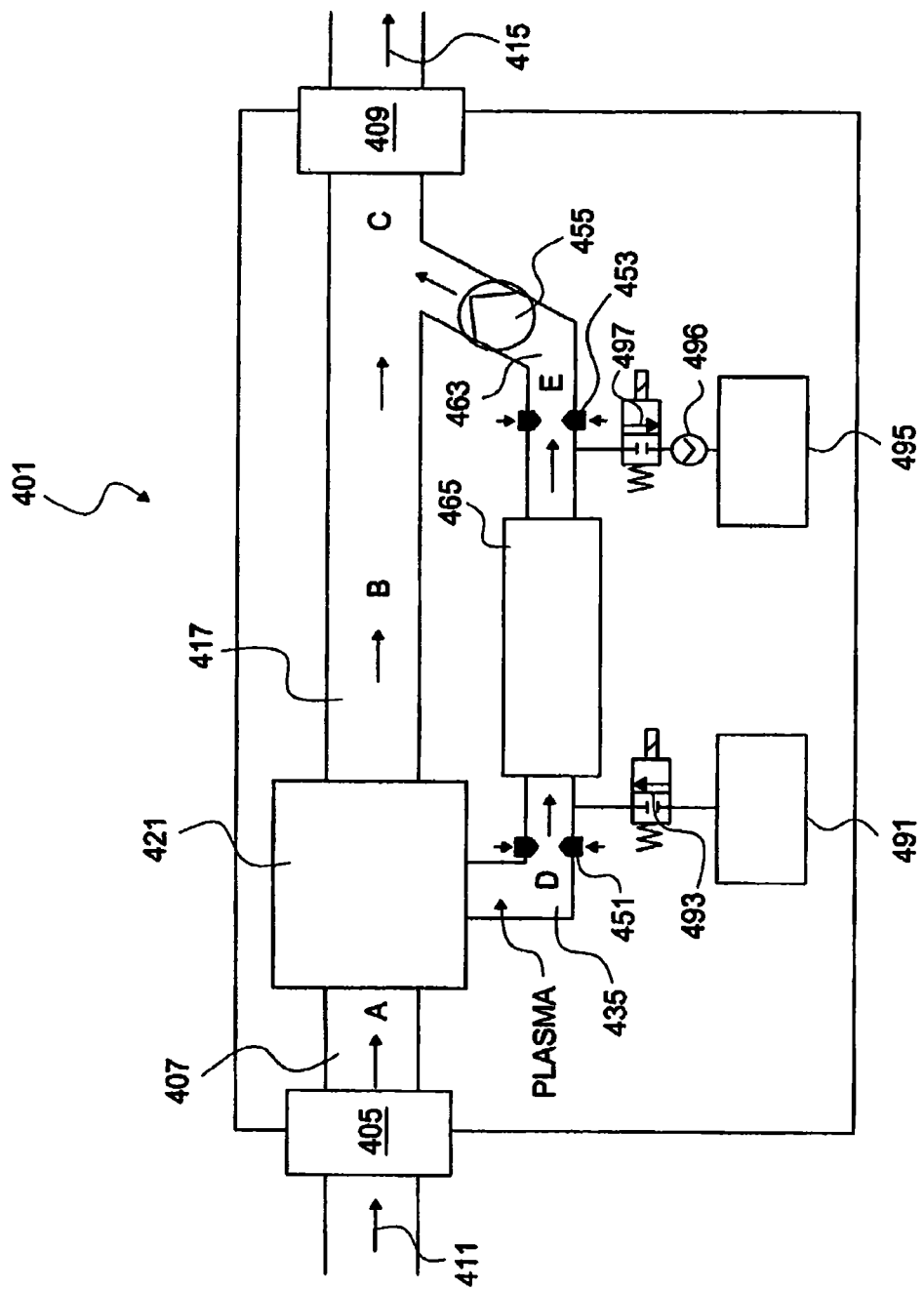
FIG. 7 is an enlarged view of the adjunctive blood detoxification unit in FIG. 6.

Advantageously the artificial kidney and method of blood treatment of the invention can also be used in conjunction with existing haemo-dialysis and peritoneal-dialysis equipment. The use of aptamers is an important aspect of the inventive concept. In case of peritoneal dialysis the dialysing fluid can be purified by using the aptamer technique of the present invention. In conjunction with traditional haemo-dialysis, specific uremic toxins, groups of uremic toxins, or precursor molecules of uremic toxins, can be removed from the blood of patients with a reduced or defective kidney function. An embodiment of the invention for use in conjunction with haemo-dialysis is schematically shown in FIGS. 6 and 7 and will be referred to as Adjunctive Blood Detoxification Unit (ABD). This embodiment, the ABD unit 401 as shown in more detail in FIG. 7, can be used as an add-on to the current haemo-dialysis equipment 402 (as shown schematically in FIG. 6). It is also possible to use the ABD apparatus 401 in conjunction with peritoneal-dialysis, or as a stand-alone and thereby technically independently of other dialysis equipment, such as 402. Use is made of existing vain access 404,406 and of the regular anticoagulation which is already part of the existing haemo-dialysis procedure. The ABD unit 401 fractionizes already anticoagulated blood and removes a number of preselected target molecules. Application of the ABD unit 401 does not need to be strictly in conjunction with each and every haemo-dialysis performed on a patient and the unit 401 can also be used even less or more frequently. A more elaborate version of the ABD unit 401 (provided with anticoagulation and fluid disposal) can possibly also be applied alternatingly with haemo-dialysis. FIG. 6 shows the ABD unit 401 in use with an existing haemo-dialysis process. The ABD unit 401 can take blood by creating a reduced pressure, in succession to the existing haemo-dialysis, as a flow 411 via an upstream fluid connection 405, and purifies the blood specifically from a number of substances. Thereafter the blood returns from a downstream fluid connection 409 of the ABD unit 401 into the return circuit 415 of the existing haemodialyzer (see FIG. 6). In principle all the blood that leaves the haemodializing apparatus (typically about 250 to about 600 ml/min), can also be conducted through the ABD Unit 401, to remove the maximum of target molecules. Nevertheless this is not absolutely necessary and depends on the desired clearance of the target molecule or molecules. A shunt 40$ can be provided as an escape route for blood, when the blood flow through the ABD unit 401 would be obstructed. FIG. 7 shows the ABD unit 401 to an enlarged scale. The unit 401 brings about a separation in which plasma is separated from blood, schematically represented as separator unit 421. Plasma is subsequently conducted through a clearance or removal compartment 465 in which specific target molecules are removed by means of aptamers or other binding molecules, like antibodies, or binding surfaces, as explained herein above. The unit 401 for adjunctive detoxification of blood, shown in FIG. 7, further has a first fluid passage 407, leading to the separator unit 421 and a continued first fluid passage 417 leading from the separator unit 421 to the downstream fluid connection 409. Also leading from the separating unit 421 is a second fluid passage 435, which is provided with a first flow control means 451, schematically represented as an optional variable flow restriction. Downstream of the first flow control means 451 the second fluid passage 435 connects to an upstream entrance of the removal compartment 465 and is also selectively connected to an EDTA component 491, containing an ethylene diamine tetra acetic acid solution, or any other $Mg^{2+}$-ion-chelating or binding compound or structure. The EDTA component 491 can be selectively connected to the second fluid passage 435 by means of an EDTA control valve 493. The removal compartment 465, with a downstream exit, connects to a continued second fluid passage 463, having a second flow control means 453, optionally in the form of a variable flow restrictor. Upstream of the second flow control means 453, but downstream of the removal compartment 465, the continued second fluid passage 463 gives access to a waste component 495 via a waste control valve 497 and a fourth flow control means in the form of a pump 496. The waste control valve 497 acts as a combined second separator and third connection. Both the EDTA component 491 and the waste component 495 are useful in the regeneration of the aptamer or aptamers used in the removal compartment 465. Additionally the continued second fluid passage 463, in a downstream direction, joins the continued first fluid passage 417, via a third flow control means 455, which can be a pump. Regeneration of the aptamer or aptamers used in the removal compartment 465 is accomplished by increasing the flow resistance of the first flow control means 451, reducing the plasma flow from the first separator unit 421. At the same time the second flow control means 453 is closed and the fourth flow control means 496 is activated to generate a fluid flow through the opened EDTA control valve 493. Thereby EDTA is drawn in from the EDTA component 491 with the reduced plasma flow through the removal compartment 465. With the second flow control means 463 in closed position, or substantially closed position, the amount of plasma that flows to the waste component 495 can be controlled, by the waste control valve 497 and the pump rate of the fourth flow control means. The flow control means 497 may also be situated at any other place in the circuit between the EDTA component 491 and the waste component 495. Further, gravity may be used to create a liquid flow in the circuit between the EDTA component 491 and the waste component 495, by which the EDTA component 491 is situated higher relative to the waste component 495. In another alternative embodiment the position of the EDTA component 491 and the waste component 495, as shown in FIG. 7 may be inversed. Thereby the regeneration flow is in a direction opposite to the plasma flow through the removal compartment 465. As a result of this inverse flow one or both of the first and second flow control means 451, 453 may be formed as simple one-way valves. It is thereby also possible to feed the EDTA by gravity and controlling the inverse regeneration flow by reversing the pumping direction of the third flow control means 455.

In respect of any of the above referred to aptamer regenerations, it can be of further advantage when the removal compartment 465 is duplicated, so that clearance of plasma can continue in one of the removal compartments, while the aptamer, or aptamers, in the other removal compartment are being regenerated.

Aptamers are oligonucleotides of RNA or DNA, which can specifically bind to target molecules (comparable to antibodies). The aptamers in the removal compartment have preferably been bound to a surface, such as to glass balls. The degree of specific disposal of certain substances can be predefined by:
(i) the absolute quantity (number of molecules) of a particular aptamer;
(ii) the proportion of the different aptamers;
(iii) the affinity (IQ of a particular aptamer;
(iv) physical and chemical parameters (flow speed, number of passes, pH, temperature, etc); and/or
(v) the number of times that the aptamers are regenerated.

Binding of an aptamer to its target molecule requires a sufficiently strong tertiary conformation (structure) of the aptamer and of the aptamer-target complex. Sufficient stability always requires $Mg^{2+}$-ions, which are already sufficiently present in the plasma. The necessary presence of $Mg^{2+}$-ions also offers the possibility of removing the bound uremic toxins in the interim. By catching $Mg^{2+}$-ions by means of EDTA (ethylene diamine tetra acetic acid), or by any other $Mg^{2+}$-ion-chelating or binding compound or structure, tertiary conformations are broken and thereby the affinity of the aptamer for its target is gone. Target molecules, i.e. uremic toxins, are disposed together with the EDTA by rinsing the removal compartment 465 once or a couple of times with plasma. The waste products which are released thereby will be caught separately. In FIG. 7 this is illustrated by means of the EDTA and Waste components 491, 495. By inclusion, in its second fluid passage 435, 463 of the clearance compartment 465 that includes at least one type of aptamer, a second control valve 497, between the second fluid passage 435, 463 and a waste component 495 can act as a combined third connection and second separator. When removing the uremic toxins and the EDTA from the removing compartment by flushing the removal compartment using the plasma stream in the second fluid passage 435, 463, as in the embodiment of FIG. 7 some important blood components may be lost to the waste component 495. If this would be a problem, it is also possibly to rinse with a physiological salt solution, in which case the second fluid passage 435, 463 can be temporarily interrupted. A modification of the apparatus 401 of FIG. 7 may then be arranged to connect a supply of physiological salt upstream of the removal compartment 465. The exact technical implementation will thus be subject to variation and need not be strictly in accordance with FIG. 7.

The regenerability of the aptamers moreover provides a possibility to catch predefined (small) molecules at the start of dialysis and to return same to the blood tract at the end of the dialysis. This can be accomplished by arranging for at least one additional liquid passage with its own removal compartment to by-pass the main removal compartment. In the secondary flow small target molecules can then be captured and be returned to the patient after completion of the dialyzing. The loss of useful molecules can thereby be reduced or prevented.

The disposable part is preferably formed as one single unit, comprising among other things hoses, removal compartment, EDTA and waste components as well as connection fittings. The unitized disposable part can be readily inserted into and be removed from the apparatus.

In selecting uremic toxins to remove, as target molecules, a number of approaches is available. Removing uremic toxins, to achieve considerably lower concentrations of these substances in the blood of patients with kidney disorders, the following three approaches are possible:
a) Molecule approach: The affinity of the aptamer is aimed against a molecule that is considered one of the uremic toxins. The aptamer has a significant affinity for only one single molecule. Using this approach aptamers can be selected against e.g. proteins and other large molecules.
b) Epitope approach: The affinity of an aptamer is aimed against a chemical structure, which is present in several molecules which are considered to belong to uremic toxins. There are e.g. fifteen guanidines that have been identified as a uremic toxin. The chemical group of the guanidines by definition has the following general structure:

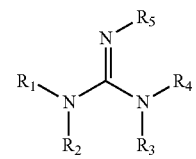

It is possible to select an aptamer with a high affinity for the common chemical structure, i.e. the epitope that is present in all guanidines. Therefore one aptamer (in an appropriate amount) is able to bind an entire group of chemically related molecules. Another example of the epitope approach is an aptamer against both p-cresol sulfate and against indoxyl sulfate, wherein the conjugate side, —$OSO_3H$, acts as a target epitope.
c) Precursor approach: It is possible to influence physiological processes by selectively removing precursor molecules. Several biochemical compounds (i.e. organic molecules) are known to be precursors of a number of uremic toxins, e.g.:
  Glyoxal as a precursor of AGE's (Advanced Glycation End products).
  Amadori-structure as precursor of AGE's.
  Guanosine (together with glucose) as precursor of $N^2$-[1-(1-carboxy)methyl]guanosine (CMG), $N^2$-[1-(1-carboxy)ethyl]guanosine (CEG), $N^2$-[1-(1-carboxy)ethyl]deoxyguanosine (CEdG) and $N^2$-[2-(1-carboxy-3,4,5-trihydroxypentyl)guanosine (CTPG).
  Xanthylic acid, via xantosine and xanthine, as precursor for uric acid.

In connection with the above described embodiments the following options can be employed either separately or in combination with one another:

Monitoring of the concentration of the target molecules. To this end specific sensors can be placed at several places in the system.

It may be desirable to prevent that too much important blood components would disappear as a result of removing the uremic toxins and the EDTA from the removal compartment by flushing the removing compartment with plasma. This can be achieved by rinsing the disposal compartment with a physiological salt solution instead.

The regenerability of the aptamers holds the possibility to catch predefined (small) molecules at the start of dialysis and to return same to the blood tract at the end of dialysis. Thereby loss of useful molecules can be reduced or prevented.

Aptamers are susceptible to degradation by exonuclease activity and by endonuclease activity. Degradation by nuclease activity may be prevented in several ways, including either individually or in combination:

Nucleases, exo-nucleases as well as endo-nucleases, present in the blood, blood plasma or plasma water are not allowed to reach the compartment or compartments where the aptamers are located, i.e. contact between nucleases and aptamers is prevented. This is effected by separating the nucleases, being proteins, from the target uremic toxins. Separation may be effected by filtration or centrifugation (aferese)—as is known in the art. One possible embodiment of the invention can include two parallel secondary liquid flows, each including a removal compartment in which the aptamers can be regenerated. One secondary flow is arranged to capture large target molecules, using chemically stabilized aptamers, and a second secondary liquid flow from which nucleases are excluded, is arranged to capture small target molecules, using chemically not stabilized aptamers.

Use of chemically stabilized aptamers. Different ways are known in the art

Selection of temperature in the aptamer compartments. Nuclease activity is diminished to a very low level outside a certain temperature range by changing the temperature in the compartment where the aptamers are located. This may be as well an increase in temperature as a decrease. The selected aptamer needs to be temperature sensitive, whereby the selected temperature is not in the vicinity or the temperature optimum for nuclease activity.

The change in temperature may be combined with a change in a second physical or chemical parameter, like the concentration or $Mg^{2+}$-ions or light, or indeed any other suitable parameter.

Exo-nuclease activity may be prevented by adding a specific chemical group at the final nucleotide (on both sides) of the aptamer, or bind the aptamer with one end or both ends to a surface.

Capture a specific nuclease, or specific nucleases, before the liquid in which the nuclease is present, enters the compartment, or compartments, in which the aptamers are located. Several techniques for this are known in the art. In case aptamers are used to capture (specific) nucleases, the nucleases may be returned to the blood stream by regeneration of the aptamers, or may be removed to waste containers.

A combination of any of the above.

The selection of aptamers that show a temperature dependency for binding to their specific target molecules, offers the possibility to regenerate the aptamers by changing the temperature. The selection or use of aptamers, which are sensitive to temperature as a physical parameter to regenerate the aptamers, may be combined with another physical or chemical parameter, like the $Mg^{2+}$-ion concentration. A possible physical parameter may be an ion that is bound to an ion exchanger, present in a liquid flow parallel to the aptamer compartment, which flow can be cut of, that are released from the ion exchanger as an ion present in the blood, blood plasma or plasma water is bound to the ion exchanger. For example $X^+$ has been bound to an ion exchanger and is released when e.g. $K^+$ is bound. Transport of the liquid containing $K^+$ is regulated. As explained above one embodiment of the invention may include parallel secondary liquid flows, each including a removal compartment in which the aptamers can be regenerated. Each secondary flow can thereby be arranged to capture differently sized target molecules, using differently stabilized aptamers.

At the exit of the ABD unit a filter is included in order to trap or catch short fragments of aptamers, i.e. oligonucleotides, or mononucleotides.

Certain aptamers may be selected in such a way, that they are not only depending on $Mg^{2+}$-ions or temperature. They may be sensitive to light or some allosteric molecule, i.e. a small organic compound, offering the possibility to regenerate them independently as a group or, by using different photosensitive chemical structures and/or different allosteric molecules, even individually.

In the so regarded waste liquid, valuable compounds may still be present in a too high concentration for removal. It may be desirable to intercept substances from plasma, plasma water or waste fluid, which would otherwise be removed to a great extend. This becomes possible by incorporation of an extra compartment in which aptamers are located, or another compound specifically binding target molecules, that bind e.g. albumin. By regeneration of the aptamer, albumin can be guided back to the blood stream.

Drugs or any other valuable compound may be removed from the blood, plasma or plasma water, by undesired binding of an epitope on the drug to an aptamer, e.g. the sulphate moiety or p-cresyl sulphate. Loss for the patient may be prevented by binding such drugs before they reach the removal compartment by using an extra compartment in which an aptamer selected against another epitope on the drug, or another compound, specifically bind the drug or drugs. Regeneration of the aptamers offers the possibility to guide the drugs back into the blood stream.

It may be important to measure to which extend certain aptamers in the removal compartment are saturated during the process of cleaning the blood of the patient. Saturation can be measured by incorporating a shunt, parallel to fluid passage 435, 463 (see FIG. 7), in which one or more sensors are fixed, sensitive to the same target molecule or target molecules. The sensor may be provided with an aptamer or any other binding structure. The signal from this sensor will be an indication of the extent of saturation of the aptamers in the removal compartment. Also, it is possible to control regeneration of the removal compartment using this sensor. If a certain degree of saturation of a particular aptamer has been reached, regeneration of the removal compartment may be automatically initiated.

In the removal compartment DNA-aptamers and RNA-aptamers may be present next to one another. As the stabilizing impact of $Mg^{2+}$ for the RNA-aptamers target molecules and for the DNA-aptamers target molecules is different, at least in some cases, the possibility exists to (semi-) selectively regenerate the aptamers.

It is thus' believed that the operation and construction of the present invention will be apparent from the foregoing description. Any reference in this specification to artificial kidney is to be understood as referring to a device for the treatment of blood, capable of performing a process, or part of a process, that is associated with the performance of a human or animal kidney. Where in this specification reference is made to 'plasma' it means the fluid portion of the blood, i.e. human or animal blood from which the cellular components have been removed, without the blood being coagulated; also some large molecules (macromolecules) may have been removed. Where this specification makes reference to 'plasma water' it means the fluid portion of the human or animal blood from which the cellular components have been removed as well as large and at least some middle and small molecular weight molecules. The invention is not limited to any embodiment herein described and, within the purview of the skilled person; modifications are possible which should be considered within the scope of the appended claims. Equally all kinematic inversions are considered inherently disclosed and to be within the scope of the present invention. The term comprising when used in this description or the appended claims should not be construed in an exclusive or exhaustive sense but rather in an, inclusive sense. Expressions such as: "means for . . . " should be read as: "component configured for . . . " or "member constructed to . . . " and should be construed to include equivalents for the structures disclosed. The use of expressions like: "critical", "preferred", "especially preferred" etc. is not intended to limit the invention. Features which are not specifically or explicitly described or claimed may be additionally included in the structure according to the present invention without deviating from its scope.

The invention claimed is:

1. A device for detoxification of one of plasma and plasma water, the device including:
    a first fluid passage having a first fluid connection defining an upstream end and a second fluid connection defining a downstream end of the first fluid passage, the first fluid passage being adapted to receive blood at its upstream end and to return blood at its downstream end;
    a second fluid passage extending from a first location in the first fluid passage to a second location in the first fluid passage;
    a separator for separating at least one of blood cells and molecules of high and medium molecular weight from blood, the separator being arranged to effect separation between the first fluid passage and the second fluid passage; and
    at least one clearance or removal compartment arranged in the second fluid passage and adapted to subject a passing fluid, including at least one of plasma and plasma water received from the separator to treatment, characterized in that
    the at least one clearance or removal compartment comprises one or more aptamers selected to remove at least one of uremic toxins, groups of uremic toxins and precursor molecules of uremic toxins from the passing fluid of plasma or plasma water, wherein the aptamers in the clearance or removal compartment are regenerated by changing a physical or chemical parameter, including at least one of the temperature, the concentration of ions, or light, or by using photosensitive chemical structures and/or allosteric molecules, and
    the second fluid passage extends from a first location adjacent to the upstream end of the first fluid passage to a second location adjacent to the downstream end of the first fluid passage, such that the fluid of plasma or plasma water treated by the at least one clearance or removal compartment can be returned directly to the blood, wherein the second fluid passage is provided with a first flow control means and downstream of the first flow control means is connected to a component for receiving an ethylene diamine tetra acetic acid solution or any other Mg2+-ion-chelating-or binding compound or structure or a physiological salt solution, which component can be selectively connected to the second fluid passage by means of a control valve, and wherein a continued second fluid passage is provided with a second flow control means and upstream of the second flow control means, but downstream of the clearance or removal compartment, the continue second fluid passage gives access to a waste component via a waste control valve and a fourth flow control means in the form of a pump.

2. The device according to claim 1, wherein the clearance or removal compartment is duplicated, so that treatment of plasma or plasma water can continue in one of the clearance or removal compartments while the one or more aptamers in the other clearance or removal compartment are being regenerated.

3. The device according to claim 1, including parallel secondary liquid flows, each including a clearance or removal compartment in which the aptamers can be regenerated.

4. The device according to claim 3, wherein a supply of physiological salt is connected upstream of the clearance or removal compartment.

5. The device according to claim 3, wherein the position of the component and the waste component is inversed.

6. The device according to claim 1, wherein the component is situated higher relative to the waste component.

7. A process of using a device according to claim 1, the process comprising:
    combining the device as an add-on device with haemodialysis equipment; and
    performing adjunctive detoxification on dialysed blood coming from the haemo-dialysis.

8. A process of using a device according to claim 1, the process comprising:
    attaching the device as an add-on device to peritoneal dialysis equipment; and
    performing adjunctive detoxification on dialyzing fluid coming from the peritoneal dialysis equipment.

* * * * *